(12) United States Patent  (10) Patent No.: US 7,643,884 B2
Pond, Jr. et al.  (45) Date of Patent: Jan. 5, 2010

(54) ELECTRICALLY INSULATED SURGICAL NEEDLE ASSEMBLY

(75) Inventors: John D. Pond, Jr., Germantown, TN (US); William Keith Adcox, Memphis, TN (US)

(73) Assignee: Warsaw Orthopedic, Inc.

( * ) Notice: Subject to any disclaimer, the term of this patent is extended or adjusted under 35 U.S.C. 154(b) by 620 days.

(21) Appl. No.: 11/047,358

(22) Filed: Jan. 31, 2005

(65) Prior Publication Data

US 2006/0173521 A1 Aug. 3, 2006

(51) Int. Cl.
*A61N 1/05* (2006.01)
(52) U.S. Cl. ..................................... 607/116
(58) Field of Classification Search .............. 607/116; 600/129
See application file for complete search history.

(56) References Cited

U.S. PATENT DOCUMENTS

| | | |
|---|---|---|
| 2,704,064 A | 3/1955 | Fizzell et al. |
| 3,364,929 A | 1/1968 | Ide et al. |
| 3,664,329 A | 5/1972 | Naylor |
| 3,682,162 A | 8/1972 | Colyer |
| 3,811,449 A | 5/1974 | Gravlee et al. |
| 3,830,226 A | 8/1974 | Staub et al. |
| 3,892,232 A | 7/1975 | Neufeld |
| 3,957,036 A | 5/1976 | Normann |
| 4,099,519 A | 7/1978 | Warren |
| 4,207,897 A | 6/1980 | Lloyd et al. |
| 4,224,949 A | 9/1980 | Scott et al. |
| 4,235,242 A | 11/1980 | Howson et al. |
| 4,285,347 A | 8/1981 | Hess |
| 4,515,168 A | 5/1985 | Chester et al. |
| 4,519,403 A | 5/1985 | Dickhudt |
| 4,545,374 A | 10/1985 | Jacobson |
| 4,573,448 A | 3/1986 | Kambin |
| 4,592,369 A | 6/1986 | Davis et al. |
| 4,633,889 A | 1/1987 | Talalla et al. |
| 4,658,835 A | 4/1987 | Pohndorf |
| 4,759,377 A | 7/1988 | Dykstra |
| 4,807,642 A | 2/1989 | Brown |
| 4,823,791 A | 4/1989 | D'Amelio et al. |
| 4,892,105 A | 1/1990 | Prass |
| 4,926,865 A | 5/1990 | Oman |
| 4,962,766 A | 10/1990 | Herzo |
| 4,964,411 A | 10/1990 | Johnson et al. |
| 4,974,595 A * | 12/1990 | Nordenstrom ............... 600/373 |
| 5,007,902 A | 4/1991 | Witt |
| 5,058,602 A | 10/1991 | Brody |
| 5,081,990 A | 1/1992 | Deletis |
| 5,092,344 A | 3/1992 | Lee |
| 5,127,403 A | 7/1992 | Brownlee |
| 5,161,533 A | 11/1992 | Prass et al. |

(Continued)

FOREIGN PATENT DOCUMENTS

WO    WO 97/26836    7/1997

(Continued)

*Primary Examiner*—Angela D Sykes
*Assistant Examiner*—Michael Kahelin

(57) ABSTRACT

A surgical needle assembly for penetrating soft and hard tissues of a patient includes a handle assembly removably coupled to the needle assembly. The needle assembly is electrically coupled to an electrical signal source. The surgical tool includes an electrically conductive portion in communication with an un-insulated distal end of the needle assembly, and an insulated portion extending from the distal end to the handle assembly.

9 Claims, 4 Drawing Sheets

U.S. PATENT DOCUMENTS

| | | |
|---|---|---|
| 5,196,015 A | 3/1993 | Neubardt |
| RE34,390 E | 9/1993 | Culver |
| 5,242,443 A | 9/1993 | Kambin |
| 5,255,691 A | 10/1993 | Otten |
| 5,282,468 A | 2/1994 | Klepinski |
| 5,284,153 A | 2/1994 | Raymond et al. |
| 5,284,154 A | 2/1994 | Raymond et al. |
| 5,313,956 A | 5/1994 | Knutsson et al. |
| 5,375,067 A | 12/1994 | Berchin |
| 5,433,739 A | 7/1995 | Sluijter et al. |
| 5,474,558 A | 12/1995 | Neubardt |
| 5,480,440 A | 1/1996 | Kambin |
| 5,482,038 A | 1/1996 | Ruff |
| 5,540,235 A | 7/1996 | Wilson |
| 5,560,372 A | 10/1996 | Cory |
| 5,566,678 A | 10/1996 | Cadwell |
| 5,579,781 A | 12/1996 | Cooke |
| 5,584,849 A | 12/1996 | Yoon |
| 5,593,429 A | 1/1997 | Ruff |
| 5,630,813 A | 5/1997 | Kieturakis |
| 5,671,752 A | 9/1997 | Sinderby et al. |
| 5,711,307 A | 1/1998 | Smits |
| 5,775,331 A | 7/1998 | Raymond et al. |
| 5,779,642 A | 7/1998 | Nightengale |
| 5,797,854 A | 8/1998 | Hedgecock |
| 5,807,275 A | 9/1998 | Jamshidi |
| 5,830,151 A | 11/1998 | Hadzic et al. |
| 5,851,191 A | 12/1998 | Gozani |
| 5,853,373 A | 12/1998 | Griffith et al. |
| 5,885,219 A | 3/1999 | Hightengale |
| 5,888,196 A | 3/1999 | Bonutti |
| 5,928,158 A | 7/1999 | Aristides |
| 5,976,094 A | 11/1999 | Gozani |
| 6,004,262 A | 12/1999 | Putz et al. |
| 6,038,477 A | 3/2000 | Kayyali |
| 6,050,992 A | 4/2000 | Nichols |
| 6,104,960 A | 8/2000 | Duysens et al. |
| 6,112,120 A * | 8/2000 | Correas ........................ 607/37 |
| 6,132,386 A | 10/2000 | Gozani et al. |
| 6,132,387 A | 10/2000 | Gozani et al. |
| 6,146,335 A | 11/2000 | Gozani |
| 6,159,179 A | 12/2000 | Simonson |
| 6,161,047 A | 12/2000 | King et al. |
| 6,224,549 B1 | 5/2001 | Drongelen |
| 6,259,945 B1 | 7/2001 | Epstein et al. |
| 6,266,558 B1 | 7/2001 | Gozani et al. |
| 6,277,094 B1 | 8/2001 | Schendel |
| 6,283,960 B1 * | 9/2001 | Ashley ........................ 606/32 |
| 6,312,392 B1 | 11/2001 | Herzon |
| 6,466,817 B1 | 10/2002 | Kaula et al. |
| 6,500,128 B2 | 12/2002 | Marino |
| 6,512,958 B1 | 1/2003 | Swoyer et al. |
| 6,554,778 B1 | 4/2003 | Fleming, III |
| 6,562,046 B2 | 5/2003 | Sasso |
| 6,564,078 B1 | 5/2003 | Marino et al. |
| 6,579,244 B2 | 6/2003 | Goodwin |
| 6,582,441 B1 | 6/2003 | He et al. |
| 6,605,085 B1 | 8/2003 | Edwards |
| 6,638,281 B2 | 10/2003 | Gorek |
| 6,796,985 B2 | 9/2004 | Bolger et al. |
| 2002/0072686 A1 | 6/2002 | Hoey et al. |
| 2002/0147485 A1 | 10/2002 | Mamo et al. |
| 2003/0028146 A1 | 2/2003 | Aves |
| 2003/0045808 A1 | 3/2003 | Kaula et al. |
| 2003/0083688 A1 | 5/2003 | Simonson |
| 2003/0105503 A1 | 6/2003 | Marino |
| 2003/0181958 A1 | 9/2003 | Dobak, III |
| 2003/0195405 A1 | 10/2003 | Marino et al. |
| 2004/0040727 A1 | 3/2004 | Miller |
| 2004/0122482 A1 | 6/2004 | Tung et al. |
| 2005/0149053 A1 | 7/2005 | Varieur et al. |

FOREIGN PATENT DOCUMENTS

| | | |
|---|---|---|
| WO | WO 00/66217 | 11/2000 |

\* cited by examiner

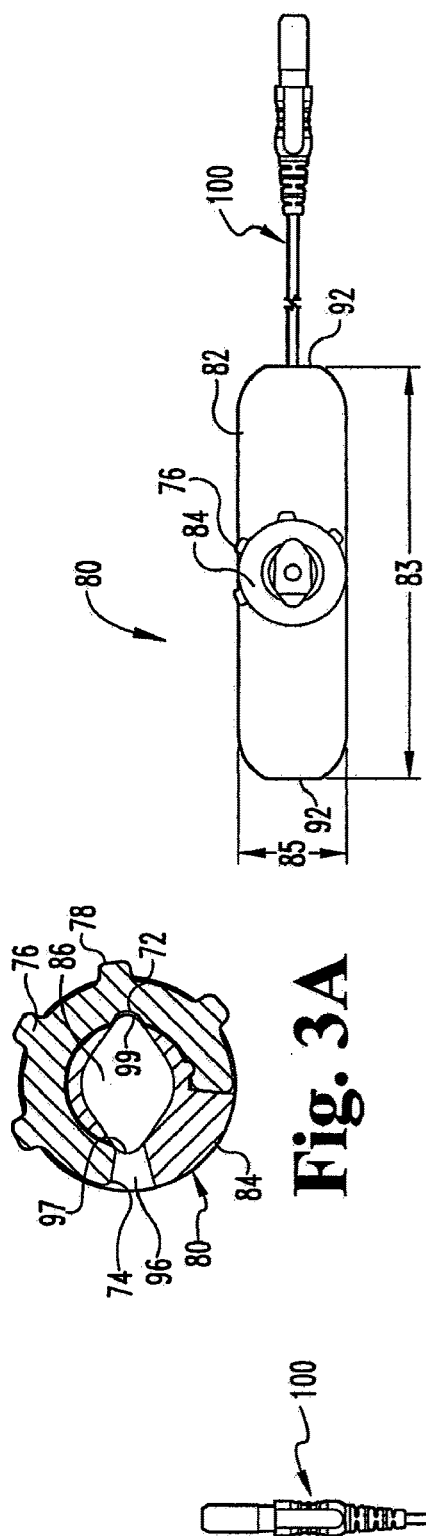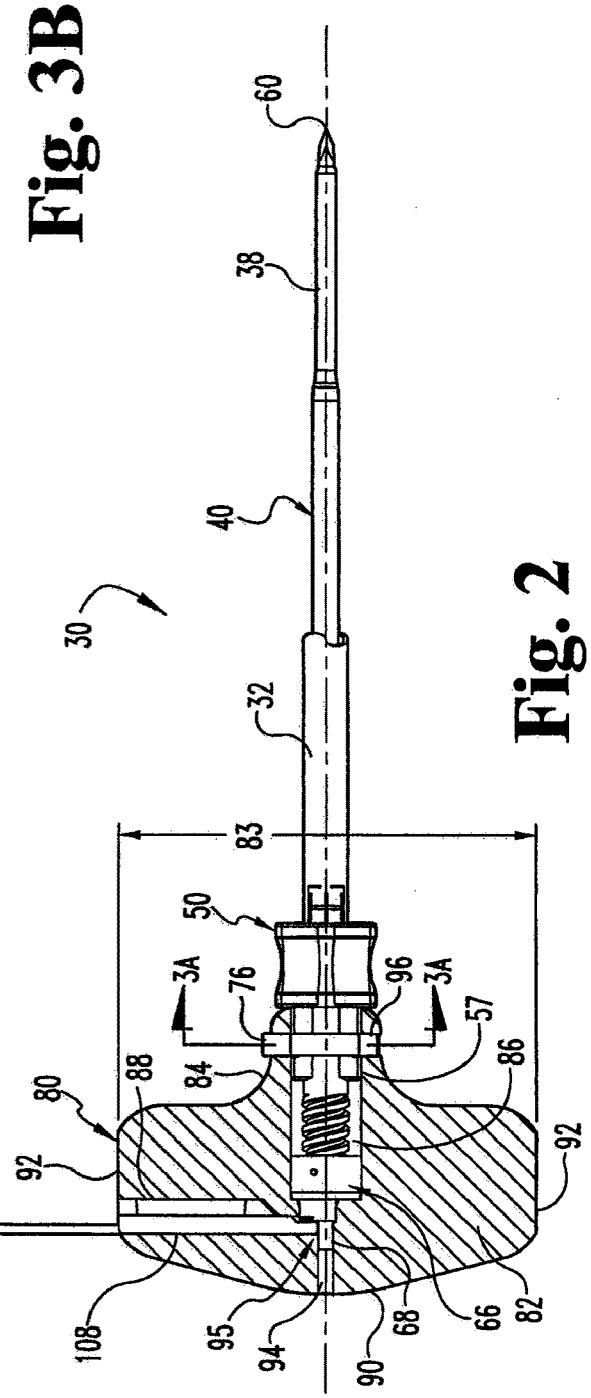

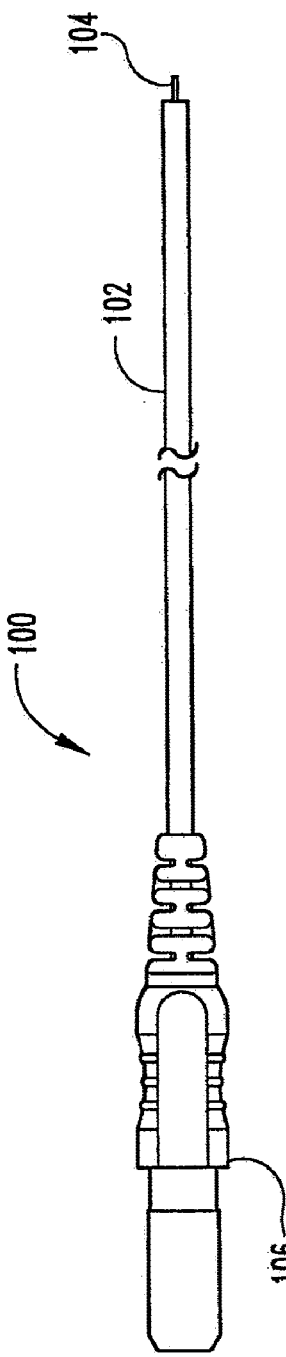
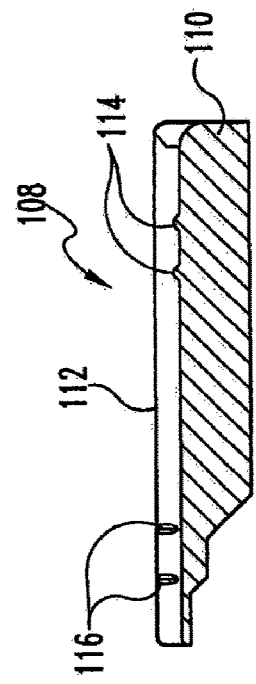
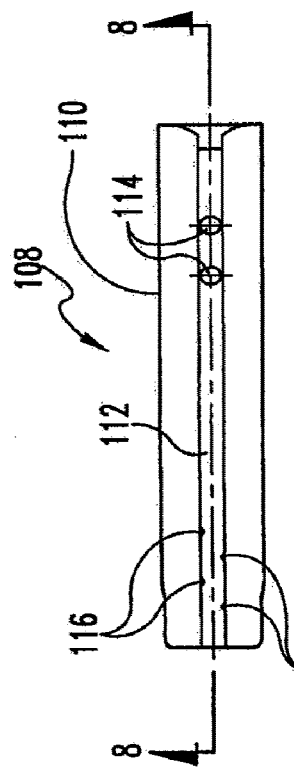

ELECTRICALLY INSULATED SURGICAL NEEDLE ASSEMBLY

BACKGROUND

Monitoring of the location of neural elements can reduce the likelihood of neural damage while accessing anatomical structures near the nerve. Systems exist which provide for delivery of an electrical current for detection of neural element proximity to a carrier of the current by visibly noting a patient's limb motor reaction when the neural element is stimulated by electrical current.

Surgical needle assemblies can be employed for access, treatment and/or delivery of treatment to locations within a patient's body. The needle assembly is inserted for penetration of soft and hard tissues of the patient during the initial steps of the treatment protocol without determining the proximity of neural elements to the needle assembly during and after such placement of the needle assembly. Subsequent treatments and procedures that are carried out based on the initial needle insertion position may impinge or interfere with the neural elements, requiring relocation of the treatment location or pathway.

SUMMARY

The present system includes a surgical tool useable by a surgeon to penetrate soft and hard tissue of the patient with a needle assembly. The needle assembly can be electrically coupled to a nerve monitoring system to allow the monitoring and detection of neural elements as the needle assembly is advanced into the patient through skin and tissue. The distal tip of the needle assembly carries the electrical signal, and the outer surface of the needle assembly is insulated to prevent shunting of the signal to tissue or instruments proximal of the distal tip. Corrective action to avoid impingement or to provide sufficient spacing from neural elements can taken during needle assembly placement, reducing the likelihood that corrective actions will need to be taken later in the surgical procedure to avoid or provide sufficient clearance with neural elements.

In one form, the needle assembly is removably engageable to a handle assembly that facilitates manipulation and control of the needle assembly as it is advanced into the patient. In one embodiment, the handle assembly is configured to allow gripping thereof by the hand of the surgeon while maintaining the electrical lead coupling the needle assembly to the nerve monitoring system out of the way of the surgeon.

In one procedure, the surgical tool is used in minimally invasive spinal surgical procedures. The needle assembly is percutaneously advanced into the patient and engaged to the pedicle of a vertebra. During such engagement, the proximity of neural elements to the distal tip is monitored to allow for corrective action to be taken to avoid or provide sufficient spacing of the needle assembly from neural elements during this initial access phase of the procedure. In one embodiment, when the needle is engaged to the pedicle at the desired location, the handle assembly is removed from the needle assembly. The needle assembly includes a cannula housing a stylet, and the stylet is removed so that the cannula remains engaged to the pedicle. A guidewire can be positioned through the lumen of the cannula, and the cannula withdrawn. The guidewire can then guide other instruments, implants or other surgical devices or instruments to the pedicle. Other procedures are contemplated at locations along the spinal column other than the pedicles, and at other locations within the body of the patient other than the spinal column.

BRIEF DESCRIPTION OF THE FIGURES

FIG. 2 is an elevation view in partial section of the surgical tool including a needle assembly coupled to a handle assembly.

FIG. 3A is a section view along line 3A-3A of FIG. 2.

FIG. 3B is a distal end view of the handle assembly of FIG. 2.

FIG. 6 is an elevation view of a lead comprising a portion of the surgical tool of FIG. 1.

FIG. 7 is an elevation view of a housing comprising a portion of the handle assembly.

FIG. 8 is a section view through line 8-8 of FIG. 7.

DETAILED DESCRIPTION OF THE ILLUSTRATED EMBODIMENTS

Figure 1:
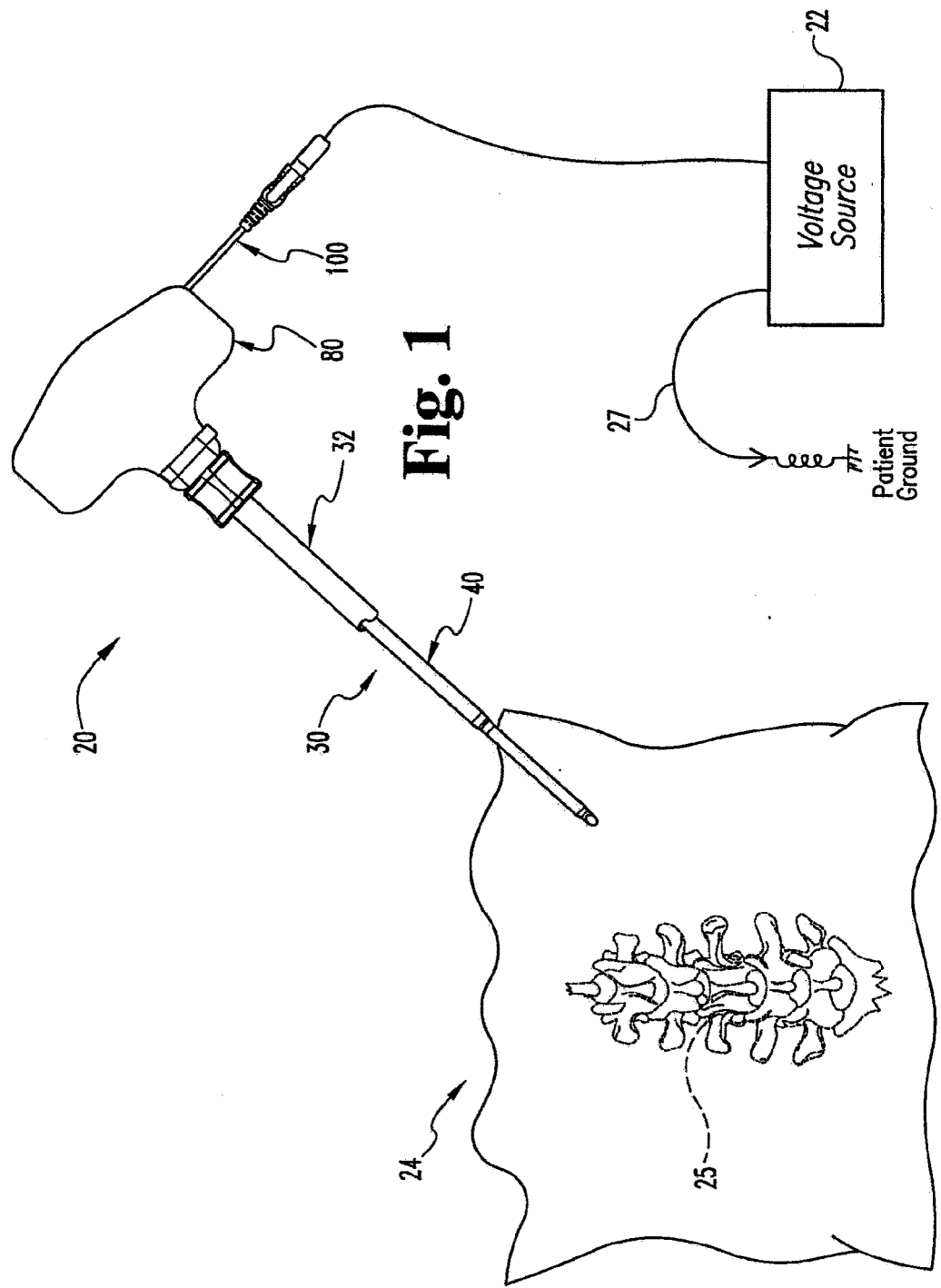
FIG. 1 is a view of the surgical field with an assembled perspective view of a surgical tool and nerve and monitoring system.

While this device is susceptible of embodiment in many different forms, there is shown in the drawings, and will herein be described in detail, several specific embodiments, with the understanding that the present disclosure can be considered as an exemplification and is not intended to be limited to the embodiments illustrated.

The present system relates to surgical tools used in accessing locations within the body of the patient while monitoring the proximity of neural elements to the tool. In one form, the surgical tool includes a needle assembly electrically engageable to a nerve monitoring system, where the needle assembly is operable to carry an electrical signal at its distal tip and allow the surgeon to monitor the proximity of neural elements with the nerve monitoring system as the needle is advanced to the target location in the patient. The proximity of the needle assembly to the neural elements can be controlled to reduce the potential neural element impact of needle insertion and subsequent procedures carried out based on the needle insertion location. The target location may include bony structures, an organ, a canal or space, a tumor or other defect, or any anatomical location or structure within a patient. The needle assembly includes a structure that facilitates operative positioning and control by the surgeon during the procedure. Once the needle has been positioned at the target location, subsequent procedures can be carried out. Such subsequent procedures can include therapy, implants, substances, or the like provided by, through or upon the needle assembly. Subsequent procedures may also include using the needle assembly as a platform or guide for subsequent placement of instruments, implants and other devices and therapeutic materials.

The needle assembly includes a distal needle structure positionable within the patient and operable to carry an electrical signal, a handle assembly, and an electrical lead. In one embodiment, the needle structure is removably engageable to the handle assembly, although embodiments where the needle assembly is integral with the handle assembly are also contemplated. The needle assembly is operable to deliver an electrical signal, such as a current, to a location in the patient's body to monitor proximity of the neural elements to the inserted end of the needle structure. The lead can extend from the handle assembly to an electrical signal source. Another lead can be used to ground the circuit. The needle assembly, when assembled with the handle assembly, can be completely insulated, except for the distal insertion end, to prevent shunting of the electrical signal to tissue or instruments located proximally of the insertion end.

Referring to FIGS. 1 and 2, there is provided view of a surgical field 24 that includes a portion of the posterior spinal column shown in hidden lines beneath the skin and tissue of a patient and surgical tool 20. Surgical field 24 includes spinal column segment 25 having a number of vertebrae therealong, it being understood that surgical tool 20 can have application in any region of the spine and in any approach to the spine. It is also understood that surgical tool 20 has application in procedures other than spinal surgical procedures.

Surgical tool 20 includes a needle assembly 30 and a handle assembly 80. Needle assembly 30 is received in a receptacle 86 extending axially into handle assembly 80. Needle assembly 30 can be electrically coupled to a nerve monitoring system 22 via lead 100 when positioned in receptacle 86. Lead 100 extends into handle assembly 80 via a lateral bore 88, where it is electrically coupled to needle assembly 30. A second reference 27 coupled to a patient (not shown) can be provided as a ground. In one procedure, the needle assembly 30 is positionable through the skin and soft and hard tissues of the patient to a surgically appropriate target location such as, for example, the pedicle of a vertebra of spinal column segment 25. Subsequent procedures and instruments for accessing the spinal column can then be employed using the needle assembly and target location obtained thereby as a minimally invasive platform for treatment and/or placement of devices and implants to treat conditions associated with the spinal column.

Needle assembly 30 includes a cannula 40 and stylet 60 removably received in a central lumen of cannula 40 along a longitudinal axis 38. Stylet 60 may include any suitable distal tip configuration, such as a trocar tip configuration as shown or a beveled tip configuration. Other embodiments contemplate a needle assembly that includes a single needle element. The needle element can be solid or cannulated. In the illustrated embodiment, handle assembly 80 is removably positioned about the proximal ends of cannula 40 and stylet 60 and engaged thereto to facilitate handling and positioning of needle assembly 30 through skin and tissue to the target location in the patient's body. An outer sheath 32 may also be provided for positioning about cannula 40 and/or stylet 60. Sheath 32 may be provided with a length extending to a distal end thereof (not shown) that extends distally beyond the distal ends of cannula 40 and/or stylet 60. Sheath 32 can facilitate pre-operative handling of needle assembly 30 to prevent, for example, accidental punctures, cutting and contamination of needle assembly 30.

Figure 4:
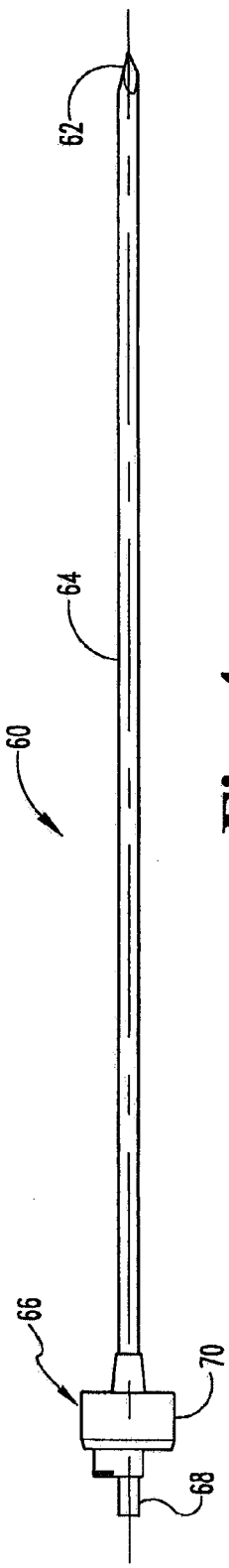
FIG. 4 is an elevation view of a stylet comprising a portion of the needle assembly of FIG. 1.

Stylet 60 is shown in isolation in FIG. 4. Stylet 60 includes a pointed tip 62 adjacent its distal end and an elongate shaft 64 extending proximally from tip 62. A hub 66 is provided at the proximal end of shaft 64. Hub 66 includes an enlarged body 70 extending radially about shaft 64, and a proximal extension 68 extending proximally from body 70.

Figure 5B:
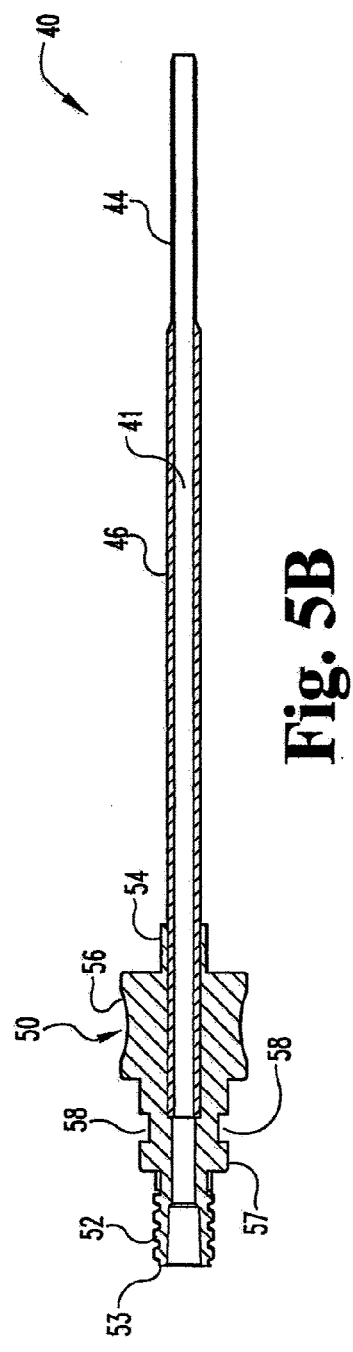
FIG. 5B is a section view along line 5B-5B of FIG. 5A.
Figure 5A:
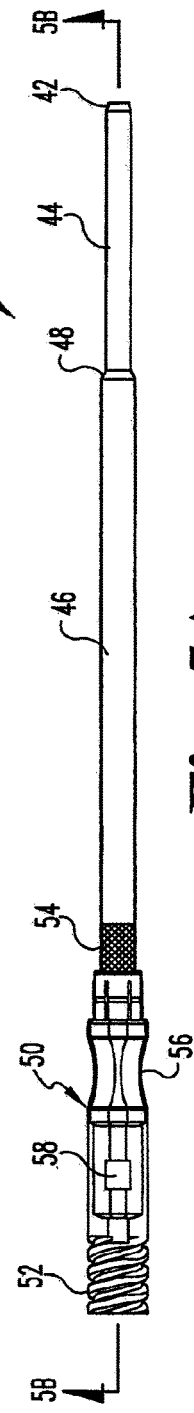
FIG. 5A is an elevation view of a cannula comprising a portion of the needle assembly of FIG. 1.

Cannula 40 is shown in FIGS. 5A and 5B. Cannula 40 includes a central lumen 41 extending therealong and opening at a distal end 42 and a proximal end 53. The outer surface area of cannula 40 may be covered or coated with a non-conductive or insulative material or member to prevent shunting of electricity from cannula 40 to adjacent tissue or instruments. A distal cannula portion 44 extends proximally from distal end 42 to a transition portion 48. Transition portion 48 extends to a proximal cannula portion 46. Proximal cannula portion 46 may include a greater outside diameter than distal cannula portion 44 to provide sufficient rigidity to cannula 40 while minimizing the size of the leading end of cannula 40. Distal end 42 may also be beveled to facilitate penetration and passage of cannula 40 through skin and tissue to the target location in the patient. Other embodiments contemplate a single diameter cannula, or a cannula with more than two diameters.

The proximal end of cannula 40 includes a connection member 50. Connection member 50 may be comprised of a non-conductive material, or of a conductive material having an insulated coating. Connection member 50 includes a proximal end fitting 52 configured to facilitate attachment of various devices to cannula 40. In one embodiment, fitting 52 provides a luer-type connection. Other embodiments contemplate other connection arrangements that are provided by fitting 52. Connection member 50 may further includes a distal sleeve portion 54 extending about proximal cannula portion 46. Distal sleeve portion 54 overlaps the insulated surface area of cannula portion 46 to ensure the cannula 40 is entirely insulated adjacent its proximal end.

Connection member 50 also includes a gripping portion 56 with opposite, laterally extending wings and concave surface depressions that allow the user to grip cannula 40 to facilitate handling when handle assembly 80 is removed. Connection member 50 also includes a proximal sleeve portion 57 extending proximally from gripping portion 56. Notches 58 are provided in opposite sides of sleeve portion 57, and as discussed further below, are engageable by a locking element to secure cannula 40 to handle assembly 80. Stylet 60 is positionable in cannula 40 so that distal tip 62 projects distally of distal end 42 when hub 66 is positioned against the proximal end of connection member 50.

Referring to FIG. 6, there is shown lead 100 that extends from handle assembly 80 and is electrically engageable to stylet 60 when stylet 60 is engaged in handle assembly 80. Link 100 includes a flexible cable portion 102 extending between a connector 106 at one end and a contact 104 at the opposite end. Connector 106 and cable portion 102 can include an outer surface layer that is plastic to facilitate cleaning and protect the conductive wiring, leads and other electrical transmission structures therein. Connector 106 can be configured for electrical engagement with a lead from a nerve monitoring system or the like such as the NIM-Spine™ System marketed by Medtronic, Inc. or any other suitable nerve monitoring system.

Contact 104 is housed within handle assembly 80, and is electrically engageable to proximal extension 68 of stylet 60 when hub 60 is positioned in handle assembly 80. In the illustrated embodiment, housing 108 is positioned in the laterally oriented bore 88 of handle 80 to secure lead 100 to handle assembly 80. Housing 108 includes a body 110 and a longitudinal trough 112 extending therealong and opening along a side of housing 108. Body 110 includes axial protrusions 114 and lateral protrusions 116 projecting into trough 112 that engage cable 102 and maintain it in position in trough 112. In particular, the opposing lateral protrusions provide restraint of cable 102 within body 110, and the axial protrusions push and facilitate frictional engagement of cable 102 against the inner surface defining bore 88. Body 110 can be engaged in bore 88 via any one or combination of a friction fit, fasteners, adhesives or welding or fusing of body 110 to handle 80.

With body 110 securely positioned in bore 88, contact 104 projects into a proximal portion 94 of receptacle 86. The proximal extension 68 of hub 60 is comprised of an electrically conductive material that contacts contact 104 in proximal portion 94 and electrically couples stylet 60 and cannula 40 to the electrical signal source.

Cannula 40 and stylet 60 may be made of stainless surgical steel or other suitable conductive material of sufficient strength to penetrate tissue of the patient to the target location. Cannula 40 and stylet 60 can be constructed from a single piece of suitable conductive material or could be constructed from more than one piece of suitable conductive material. Cannula 40 is provided with an insulated surface area between its distal and proximal ends that can be achieved through the use of a coating, e.g. polyamide coating or through other means, such as an overlaying sleeve of foam or other material. The insulated surface area ensures the electrical signal is directed to the target area adjacent the distal ends of stylet 60 and needle 40 and is not shunted to surrounding, unintended, tissue or surgical instruments.

Handle assembly 80 is shown in FIGS. 2 and 3A-3B. Handle assembly 80 comprises a handle body 82 with an electrically insulated surface area 90 and an electrically conductive area 95 internal to handle body 82. Access to electrically conductive area 95 is provided via a distally opening receptacle 86 in a distally extending neck portion 84 of handle body 82. Neck portion 84 includes a channel 96 that receives a locking element 76. A lateral bore 88 extends transversely to and opens at a lateral surface 92 of handle body 82. Lead 100 is positioned in bore 88.

Handle body 82 of handle assembly 80 includes a proximal gripping portion formed to include a major dimension 83 and a minor dimension 85. The major and minor dimensions 83, 85 are measured orthogonally to one another and orthogonally to an extension of longitudinal axis 38 through handle body 82. In one embodiment, the major dimension is at least 50% greater than the minor dimension. The provision of handle body 82 with a gripping portion having such major and minor dimensions in this manner accommodates the hand of the surgeon or other attendant, and facilitates manipulation and control of needle assembly 30 with handle assembly 80. The proximal end of body 82 includes continuously curved outer surfaces at its interface with the user's hand. This enables a user to have a secure and comfortable grasp on the handle assembly 80. Furthermore, bore 88 extends along the major dimension to position lead 100 away from the gripping surfaces of body 82. Lead 100 exits one of the lateral surfaces 92 to prevent lead 100 from interfering with gripping and control of needle assembly 30.

In another embodiment, lead 100 is engageable with an outlet or receptacle provided adjacent lateral surface 92. The outlet or receptacle is electrically coupled to needle assembly 30 in handle assembly 80.

Channel 96 in neck portion 84 opens into axially extending receptacle 86 formed in handle body 82. Receptacle 86 can include a distal portion that has the same cross-sectional size and shape as the proximal end hub 66 provided on stylet 60. In addition, the proximal end connection member 50 of cannula 40 includes a proximal sleeve portion 57 having the same size and shape as receptacle 86. The form fitting engagement between receptacle 86 and fitting 50 and hub 66 prevents rotation and provides a secure connection that eliminates movement between needle assembly 30 and handle assembly 80. In the present embodiment, receptacle 86 has an oblong shape that is asymmetric. As a result, receptacle 86 will receive the proximal end portions of stylet 60 and cannula 40 when in proper alignment with the shape of receptacle 86.

When assembled, proximal sleeve portion 57 of connection member 50 of cannula 40 occupies receptacle 86 adjacent channel 96, and notches 58 of sleeve portion 57 are aligned relative to channel 96. Cannula 40 is secured in receptacle 86 by locking element 76 in channel 96. In one embodiment, stylet 60 is press fit into receptacle 86 for engagement with handle assembly 80 so that proximal extension 68 of stylet 60 extends into a smaller proximal portion 94 of receptacle 86 and maintains a constant electrical connection with contact 104 of lead 100, thereby electrically coupling lead 100 to needle assembly 30.

In another embodiment, stylet 60 is removable from handle assembly 80 and also removable from cannula 40. In this embodiment, the electrical connection between lead 100 and stylet 60 can be maintained by any conventional means known to a person skilled in the art, such as a spring made of a conductive material. Such a spring could be mounted in bore 88 or receptacle 86, such that it makes contact with a conductive area of stylet 60 or cannula 40 when attached to handle assembly 80. The releasable connection also does not interfere with removal of handle assembly 80 from needle assembly 30 when it is desired to withdraw stylet 60 from cannula 40.

In the illustrated embodiment, channel 96 comprises a shallow channel extending circumferentially about neck portion 84, and extends approximately three-quarters of the way around neck portion 84. Channel 96 includes through-holes 97, 99, which are located opposite from one another and open into side portions of receptacle 86. Channel 96 begins at first through-hole 97, and extends counterclockwise approximately one-quarter revolution past second through-hole 99 where it terminates.

Locking element 76 can be in the form of a substantially flat, semicircular member having an aperture diameter slightly larger than the inner diameter of channel 96. Locking element 76 an outer gripping surface 78, which facilitates rotation of locking element 76 by the user. Locking element 76 is adapted to fit within channel 96 and has an outer circumference extending slightly less than three-quarters around neck portion 84.

Locking element 76 can be manipulated and rotated within channel 96 about a small angular displacement on the order of one-eighth of one rotation. This effectively allows for locking element 76 to be toggled between two positions, which correspond to the locked and unlocked configurations relative to handle assembly 80. When locking element 76 is rotated counterclockwise, no portions of locking element 76 protrude through through-holes 97 and 99, as shown in FIG. 3A, and locking element 76 does not obstruct receptacle 86. In this configuration, a groove 72 of locking element 76 is aligned with second through-hole 99, and on the other side of channel 96, the end 74 of locking element 76 is located slightly counterclockwise of second through-hole 97. This position corresponds to the unlocked orientation which allows removal and insertion of cannula 40 and hub 60 relative to handle assembly 80. Alternatively, when locking element 76 is rotated clockwise as far as possible, groove 72 is no longer aligned with through-hole 99, thereby causing a portion of locking element 76 to protrude through through-hole 99 and obstruct one side portion of passage 86. Additionally, the end 74 of locking element 76 now protrudes through the other through-hole 97, obstructing the other side portion of passage 86. This position of locking element 76 corresponds to the locked orientation which engages cannula 40 in handle assembly 80.

In order to join handle assembly 80 to cannula 40, connection member 50 is inserted through the distal opening of receptacle 86 of handle assembly 80 when locking element 76 is in the unlocked orientation. If locking element 76 is in the locked orientation, then side portions of receptacle 86 will be obstructed by locking element 76 at through-holes 97, 99, thereby preventing full insertion of cannula 40 into handle assembly 80. When proximal sleeve portion 57 is fully inserted into passage 86, enlarged gripping portion 56 will abut the distal end of neck portion 84 of handle assembly 80, and notches 58 in sleeve portion 57 will be aligned with through-holes 97, 99.

Proximal extension 68 of stylet 60 is electrically engaged with contact 104 of lead 100 in handle assembly 80. Once the proximal portion of cannula 40 has been fully inserted into receptacle 86, the user may then lock handle assembly 80 to needle assembly 30 by rotating locking element 76 clockwise relative to its FIG. 3 orientation. As locking element 76 is rotated from its unlocked position to its locked position, needle assembly 30 is fixed in place within receptacle 86. Portions of locking element 76 protrude through through-holes 97, 99 into notches 58 to secure at least cannula 40 of needle assembly 30 in position relative to handle assembly 80. The user of needle assembly 30 can use a large amount of force, if necessary, to manipulate and penetrate needle assembly 30 through tissue and/or bone, without undesired movement of needle assembly 30 relative to handle assembly 80.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A surgical tool for penetrating tissue and monitoring the proximity of neural elements, comprising:
   a needle assembly extending along a longitudinal axis, said needle assembly comprising:
      a stylet including an electrically conductive portion near a pointed distal end, a shaft extending proximally from said distal end providing a conductive path to a proximal extension of said stylet;
      a cannula including an electrically conductive portion and an insulated outer surface area around said electrically conductive portion extending along a length of said cannula wherein said pointed distal end of said stylet projects distally from said insulated surface area when said stylet is positioned in said cannula;
   a handle assembly attachable near said proximal end of said needle assembly comprising:
      an electrically insulated outer surface area;
      an electrically conductive area internal to said electrically insulated surface area and engageable with said proximal extension of said stylet;
      said handle assembly including a gripping portion having a major dimension at least 50% greater than a minor dimension, said major and minor dimensions being measured orthogonally to said longitudinal axis and to one another; and
      an electrical lead extending from said electrically conductive area through said handle assembly along said major dimension, wherein said handle assembly includes a handle body having a bore extending along said major dimension from a lateral outer surface of said handle body to a receptacle aligned along said longitudinal axis of said needle assembly when said handle assembly is engaged to said needle assembly, said lead extending through said bore, and the handle assembly further comprising a housing positioned in said bore, said housing defining a trough extending along a length of said housing with said trough opening along one side of said length of said housing, said housing further including opposite lateral protrusions projecting into said trough to secure a cable portion of said lead to said housing in said trough and an axial protrusion extending into said trough that secures said cable through said opening along said one side of said housing against an inner surface of said handle body that defines said bore, wherein said cable portion includes an electrical contact extending from the cable portion into said receptacle within said handle assembly and said proximal extension of said stylet fits inside said receptacle in said handle assembly and is electrically coupled to said electrical contact.

2. The surgical tool of claim 1, wherein said cannula includes a distal end positioned proximally of said distal pointed end of said stylet when said stylet is positioned in said cannula.

3. The surgical tool of claim 2, wherein said cannula includes a connection member on a proximal end thereof and said stylet includes a hub about a proximal end of said stylet positionable in abutting engagement with a proximal end of said connection member of said cannula.

4. The surgical tool of claim 3, wherein said hub includes a body extending about said shaft and said proximal extension of said stylet extends proximally from said body.

5. The surgical tool of claim 3, wherein said connection member on said cannula includes a gripping portion projecting outwardly from said cannula, a first sleeve portion extending about said cannula distally of said gripping portion, and a second sleeve portion about said cannula proximally of said gripping portion.

6. The surgical tool of claim 5, wherein said second sleeve portion includes a pair of notches for receiving a locking element to couple said needle assembly to said handle assembly when said hub and said connection member are at least partially received in said handle assembly.

7. The surgical tool of claim 1, wherein said cannula includes a distal end beveled to facilitate movement of said cannula through tissue of the patient.

8. The surgical tool of claim 1, wherein said cannula includes a lumen having a generally constant size between distal and proximal ends of said cannula.

9. The surgical tool of claim 1, wherein said lead extends along said major dimension of said handle assembly and exits said handle assembly at a location distally of a proximal end of said gripping portion to avoid interfering with the user's hand positioned about said gripping portion.

* * * * *

UNITED STATES PATENT AND TRADEMARK OFFICE
CERTIFICATE OF CORRECTION

PATENT NO. : 7,643,884 B2  Page 1 of 1
APPLICATION NO. : 11/047358
DATED : January 5, 2010
INVENTOR(S) : Pond, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1094 days.

Signed and Sealed this

Sixteenth Day of November, 2010

David J. Kappos
*Director of the United States Patent and Trademark Office*